(12) United States Patent
Kanare

(10) Patent No.: US 7,231,815 B2
(45) Date of Patent: Jun. 19, 2007

(54) RELATIVE HUMIDITY PROBE FOR CONCRETE

(75) Inventor: Howard M. Kanare, Wilmette, IL (US)

(73) Assignee: Construction Technology Laboratories, Inc., Skokie, IL (US)

( * ) Notice: Subject to any disclaimer, the term of this patent is extended or adjusted under 35 U.S.C. 154(b) by 199 days.

(21) Appl. No.: 11/001,729

(22) Filed: Dec. 2, 2004

(65) Prior Publication Data

US 2006/0117833 A1  Jun. 8, 2006

(51) Int. Cl.
*G01N 5/02* (2006.01)
(52) U.S. Cl. .......................... 73/73; 73/29.05
(58) Field of Classification Search ............... 73/73, 73/29.01, 29.05; 324/696
See application file for complete search history.

(56) References Cited

U.S. PATENT DOCUMENTS

| | | | |
|---|---|---|---|
| 2,017,376 A | | 10/1935 | Rother et al. |
| 3,581,197 A | * | 5/1971 | Morey et al. ............... 324/690 |
| 3,680,364 A | | 8/1972 | Carrier |
| 3,788,128 A | | 1/1974 | Strohecker |
| 3,870,951 A | | 3/1975 | Brown et al. |
| 3,927,370 A | * | 12/1975 | De Bough ................. 324/696 |
| 3,968,428 A | * | 7/1976 | Numoto ...................... 324/694 |
| 4,020,417 A | * | 4/1977 | Brehob et al. ............. 324/694 |
| 4,069,716 A | * | 1/1978 | Vanasco et al. ........... 73/432.1 |
| 4,268,824 A | | 5/1981 | Phillips et al. |
| 4,399,404 A | * | 8/1983 | Resh ........................ 324/689 |
| 4,445,788 A | | 5/1984 | Twersky et al. |
| 4,514,722 A | * | 4/1985 | Batcheler et al. .......... 340/604 |
| 4,543,820 A | * | 10/1985 | Handy et al. ................. 73/84 |
| 4,567,563 A | * | 1/1986 | Hirsch ....................... 700/284 |
| 4,711,244 A | * | 12/1987 | Kuzara ...................... 600/306 |
| 4,868,491 A | * | 9/1989 | Black ........................ 324/694 |
| 4,929,885 A | | 5/1990 | Dishman |
| 5,023,560 A | | 6/1991 | Gallagher |
| 5,382,908 A | | 1/1995 | Forsstrom et al. |
| 5,488,312 A | * | 1/1996 | Havener et al. ............ 324/689 |
| 5,621,391 A | * | 4/1997 | Elseth ....................... 340/604 |
| 5,730,024 A | | 3/1998 | Sahlen |
| 6,076,396 A | | 6/2000 | Dadachanji et al. |
| 6,422,061 B1 | * | 7/2002 | Sunshine et al. ........... 73/29.01 |
| 6,553,813 B2 | | 4/2003 | Rynhart et al. |
| 6,601,440 B1 | | 8/2003 | Chuang |
| 6,700,395 B1 | * | 3/2004 | Perry ......................... 324/696 |
| 6,793,146 B2 | * | 9/2004 | Cunkelman et al. ....... 236/44 A |

(Continued)

FOREIGN PATENT DOCUMENTS

DE    1037136 A1    8/1958

(Continued)

*Primary Examiner*—Hezron Williams
*Assistant Examiner*—John Fitzgerald
(74) *Attorney, Agent, or Firm*—Foley & Lardner LLP

(57) ABSTRACT

A probe for determining the relative humidity and temperature of a substance such as a concrete floor. The probe is adapted to be inserted into a hole in the substance being tested. The probe has a head portion and a tail portion. A display is provided on the head portion to provide a user with a visual indication of the relative humidity and temperature within the substance. The entire probe structure is designed to be contained within the hole without the need for any components protruding out of the hole to cause an obstruction.

7 Claims, 7 Drawing Sheets

U.S. PATENT DOCUMENTS 6,975,236 B2 * 12/2005 Staples ................. 340/602
2004/0140902 A1    7/2004 Staples

FOREIGN PATENT DOCUMENTS

| DE | 4427244 A1 | 2/1996 |
| GB | 653193 A | 5/1951 |
| GB | 2353360 A | 2/2001 |
| JP | 01242948 A | 9/1989 |
| JP | 11 304764 A | 11/1999 |
| JP | 2004 279394 A | 12/2003 |
| WO | WO 2004/102187 A | 11/2004 |

* cited by examiner

FIG. 1

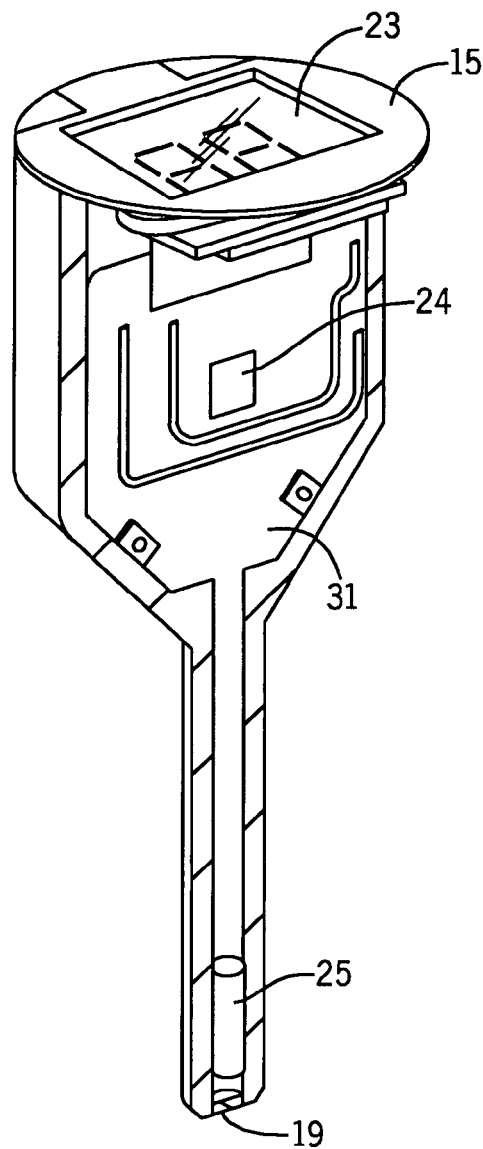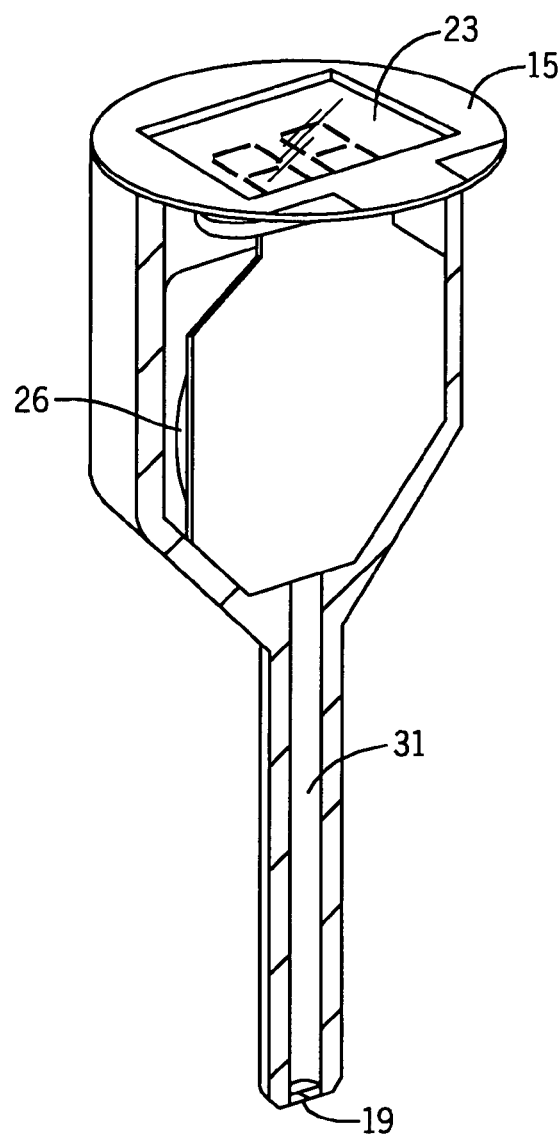
FIG. 4
FIG. 5

RELATIVE HUMIDITY PROBE FOR CONCRETE

BACKGROUND OF THE INVENTION

The present invention relates generally to the field of humidity probes, and more particularly to relative humidity probes for concrete.

Concrete is a common substrate for many commercial, industrial, and residential floors. Many types of floor coverings including wood, carpet, vinyl tile, sheet vinyl, and linoleum are commonly placed on concrete floors. Coatings such as epoxies, polyurethanes, and polymer-terrazzo, are widely used in commercial, governmental, educational, manufacturing, and health care facilities. These types of floor coverings are sensitive to moisture and prone to failure when excessive moisture is present. In addition to the floor covering materials, many modern water-based adhesives are prone to failure when excessive moisture and high pH are present. Furthermore, moisture also promotes fungal growths that can create significant odor and health problems. Typical moisture-related failures of floor coverings are curling, cupping, doming, shrinkage, blistering, and adhesion loss, all potentially leading to trip-and-fall hazards. In retail establishments, adhesive oozing at tile seams is unsightly and attracts dirt, leading to cleaning problems. In previous decades, the most commonly used asphaltic cut-back adhesives for vinyl tile were relatively insensitive to moisture. Polymer coatings and polymer terrazzo fail via osmotic blistering. Excessive moisture in concrete floors often delays construction, the installation of finish flooring and furniture, and ultimately occupancy, creating major problems for the floor covering and coatings industries.

To avoid moisture problems, floor covering and coating manufacturers specify a maximum moisture vapor emission rate (MVER) for concrete floors on which their products will be installed. The industry standard MVER specification is 3 to 5 lb./1,000 sq. ft./24 hrs. when measured by ASTM F1869, Standard Test Method for Measuring Moisture Vapor Emission Rate of Concrete Subfloor Using Anhydrous Calcium Chloride. This test is widely used: manufacturers of test kits have indicated that more than 300,000 test kits are sold annually in the United States. However, this test method has many interferences and shortcomings. Recognizing these problems, ASTM Committee F-6 on Resilient Floor Coverings adopted ASTM F2170-02, Standard Test Method for Determining Relative Humidity in Concrete Floor Slabs Using in situ Probes. This test method employs an electronic humidity sensor placed into a drilled hole in concrete, connected by a cable to a hand-held meter. This method was drawn from recent experience in Scandinavia and England, where relative humidity measurements in floors have been used for two decades. Building codes and Codes of Practice for installation of flooring in Europe have standards based on relative humidity. Flooring manufacturers in the United States are aware of this test method and are beginning to publish requirements for moisture as measured by relative humidity probes.

Commercially available relative humidity probes suffer from several drawbacks. First, they require time to equilibrate with the surrounding concrete. ASTM F2170 currently requires that drilled holes sit undisturbed for 72 hours before measurement, based on work at the Swedish Center for Building Research (Molina, 1990) and Lund University (Hedenblad, 1997). The larger the diameter of hole drilled, the longer the time necessary for the hole to equilibrate. Currently available probes require this long waiting period because the probes are of relatively large diameter: when a 16 millimeter diameter hole is drilled approximately 50 millimeters into concrete to accommodate the probe, the heat generated by drilling disturbs the moisture equilibrium in the region of the drilled hole. Time is required for the hole to re-equilibrate at service temperature and for moisture to equilibrate by diffusion within the region of the hole. Second, the "dead volume" within these probes, due to their size, requires time for moisture to diffuse and equilibrate within the probes. Third, temperature differences between the probe and the concrete require time for equilibration due to the heat capacity of the probes. All of these factors require the testing agency to wait several days to obtain test results, often when construction schedules are tight. Many of these problems stem from the relatively large size of current probes being used.

A second problem is that the current generation of instruments meeting ASTM F2170 have RH probes that are placed in concrete and separate hand held meters to which they are connected to obtain results. The meters are bulky, expensive, and can only be used with one RH probe at a time. One brand of meter requires that calibration factors for each probe be manually entered into the hand held meter one-at-a-time before use, and only up to ten such factors can be accommodated in the meter. A user must be familiar with the handheld meter to be able to determine the relative humidity.

A third problem is that the current generation of probes all protrude from the drilled holes in the concrete, making them susceptible to damage from construction traffic or building usage, or even present safety dangers to construction workers or other passersby. Probes often are broken or damaged beyond repair due to this problem. In addition, this protrusion makes current probes unsuitable for long term use or for intermittent use throughout the life of a building.

A fourth problem is that the probes require cylindrical sleeves be inserted into the holes to shield the probes from concrete except at the bottom of the hole where it is desired to make the RH measurement. Sleeves must be purchased separately and carried to the jobsite for installation. Sleeves wear out after several uses and must be replaced.

Thus, there is a need for a probe able to make accurate relative humidity measurements following the procedures outlined in ASTM F2170, but make them much more rapidly and conveniently, with less likelihood of damage to the RH measuring devices.

It is to be understood that both the foregoing general description and the following detailed description are exemplary and explanatory only, and are not restrictive of the invention as claimed.

SUMMARY OF THE INVENTION

The present invention solves the several problems of prior art probes enumerated above. In one embodiment, the present invention relates to a humidity probe having a housing with a head portion and a tail portion. An electronics module is disposed within the housing. Associated with the head portion and in communication with the electronics module is a display. A relative humidity sensor is disposed within the tail portion of the housing and in operative communication with an exterior environment and the electronics module.

In another exemplary embodiment, the present invention relates to a method of determining properties of a substance, such as concrete. The method includes the step of boring a hole having a bottom and a top in the substance. A probe having a display is inserted into the hole. The probe is positioned so that it is substantially disposed within the hole with the display located at the top of the hole. A relative humidity of the substance at the bottom of the hole is determined and displayed on the display.

In another exemplary embodiment, the present invention relates to a kit for boring a hole in a substance and determining relative humidity therein. The kit includes a drill bit having a lead portion and a reamer portion. The kit further includes a probe. The probe has a housing having an elongated portion and a head portion. An electronics module is disposed within the housing. A display, which is in communication with the electronics module, is located in the head portion. A relative humidity sensor is disposed within the elongated portion of the housing and in operative communication with an exterior environment and the electronics module. The drill bit is adapted to drill a lead hole and counterbore corresponding to the elongated portion and head portion respectively wherein the probe is countersunk within the hole.

BRIEF DESCRIPTION OF THE DRAWINGS

These and other features, aspects, and advantages of the present invention will become apparent from the following description, appended claims, and the accompanying exemplary embodiments shown in the drawings, which are briefly described below.

FIG. 1 illustrates a cross-sectional view of one embodiment of a probe in accordance with the principles of the present invention;

FIG. 4 illustrates a cross sectional view of a probe of the present invention, depicting a first half;

FIG. 5 illustrates a cross sectional view of the probe of the FIG. 4, depicting the remaining half;

DETAILED DESCRIPTION OF THE PREFERRED EMBODIMENTS

The present invention relates to a relative humidity probe having a small form factor for placement within a sampling hole in a material, thus being less susceptible to damage while in use than prior art sensors. The present invention comprises a relative humidity sensor with an integrated cylindrical sleeve and an integrated output display, all in one object to allow the device to rest below the surface of the substance being tested, such as below the surface of a concrete floor.

Figure 1:
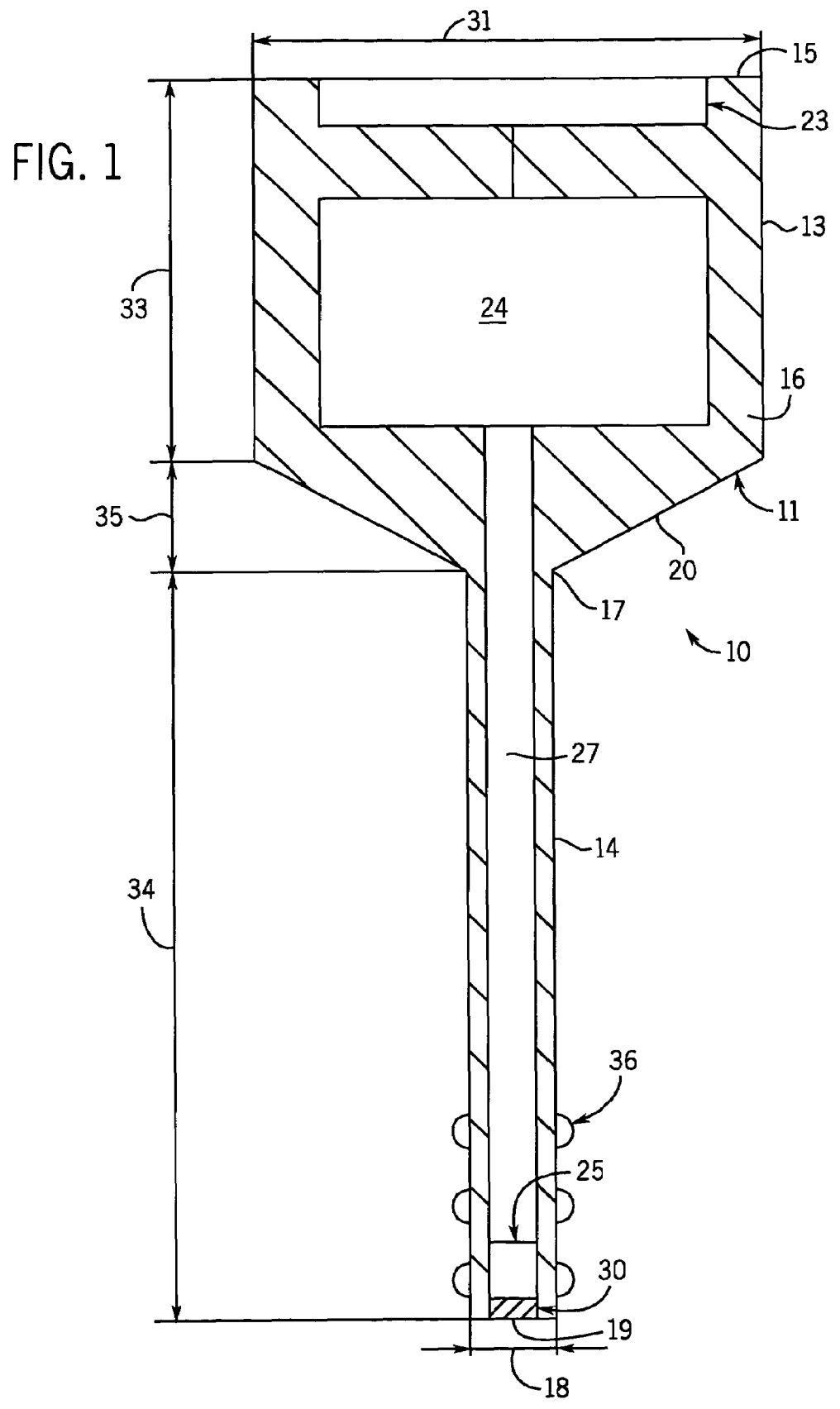
Figure 2:
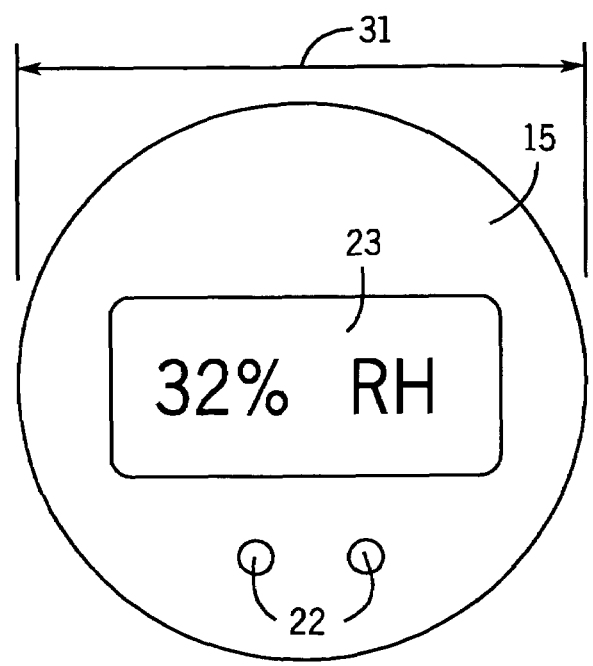
FIG. 2 illustrates a top view of the probe of FIG. 1.
Figure 3:
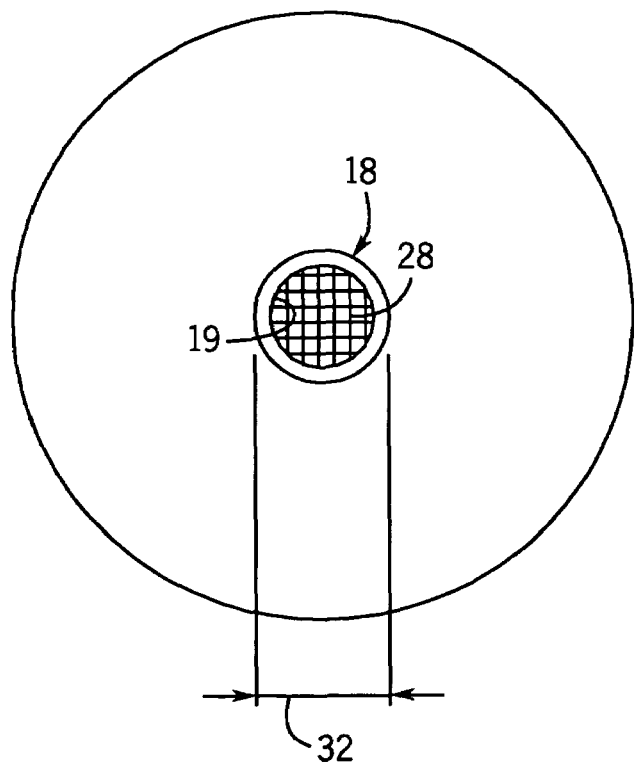
FIG. 3 illustrates a bottom view of the probe of FIG. 1.

Referring to the figures, one embodiment of a relative humidity sensor probe in accordance with the principles of the present invention is illustrated in FIGS. 1-3. As shown in FIG. 1, the probe 10 comprises a housing 11 forming an outer shell within which the components of the probe 10 are disposed. The housing 11, itself, has a head portion 13 and an elongated or tail portion 14. The head portion 13 has a top end 15 and connecting end 16. The top end 15 is, when the probe is in use, facing out of the hole so as to be visible to a user. The connecting end 16 is connected to the tail portion 14. The tail portion 14 has a detection end 18 and a connecting end 17 which is connected to the connecting end 16 of the head portion 13. The detection end of the tail portion 14 includes an aperture 19 through which a relative humidity sensor 25 (discussed below) is in communication with the environment outside of the probe 10.

In one preferred embodiment, the housing 11 has a circular cross section. In an exemplary embodiment, the head portion 13 has a diameter different from that of the tail portion 14. Preferably, the head portion 13 has a diameter greater than the tail portion 14. In one exemplary embodiment, the head portion 13 has a diameter substantially larger than the diameter of the tail portion 14. In one embodiment, the head portion 13 has a diameter of about 20 millimeters and the tail portion 14 has a diameter of about 4 millimeters. Thus, in one embodiment, the probe 11 has the tail portion 14 (i.e., probe tip) that is approximately one-fourth the diameter of existing probes, thus requiring a drilled hole that is only one-fourth the surface area and one-sixteenth the volume required by current instruments. Thus, drilled holes of the present invention are smaller in diameter and equilibrate rapidly, a feature much desired for concrete moisture testing.

In one embodiment, the head portion 13 and the tail portion 14 are connected via a tapered region 20. The tapered region transitions from having a perimeter equal to the perimeter of the connecting end 16 of the head portion 13 to a perimeter equal to the perimeter of the detection end 18 of the tail portion 14.

In an exemplary preferred embodiment, the head portion 13 has a height which is less than the height of the tail portion 14. In one embodiment, the head portion 13 has a height which is less than about half of the height of the tail portion 14. In one embodiment, the taper region 20 has a height less than that of the head portion 13. In one embodiment, the head portion 13 has a height of about 15 millimeters, the tail portion 14 has a height of about 30 millimeters, and the tapered region 20 has a height of about 5 millimeters.

The head portion 13 contains a display 23. In one exemplary embodiment, the display 23 is disposed within the head portion 13 of the housing 11. In another exemplary embodiment, the display 23 is disposed on top of the head portion 13. The display 23 is adapted to provide a visual indication of the relative humidity determined by the probe 10. In an exemplary embodiment, the display 23 is further adapted to provide visual indication of other information such as temperature (in degrees Celsius or degrees Fahrenheit), time, date, location identification number, probe identification number. In one preferred embodiment, the display 23 is a liquid crystal display (LCD). In another embodiment, the display 23 is a Light Emitting Diode (LED) type display. Various other types of display technologies can be used in accordance with the principles of the present invention without departing from the scope of the invention.

Figure 7:
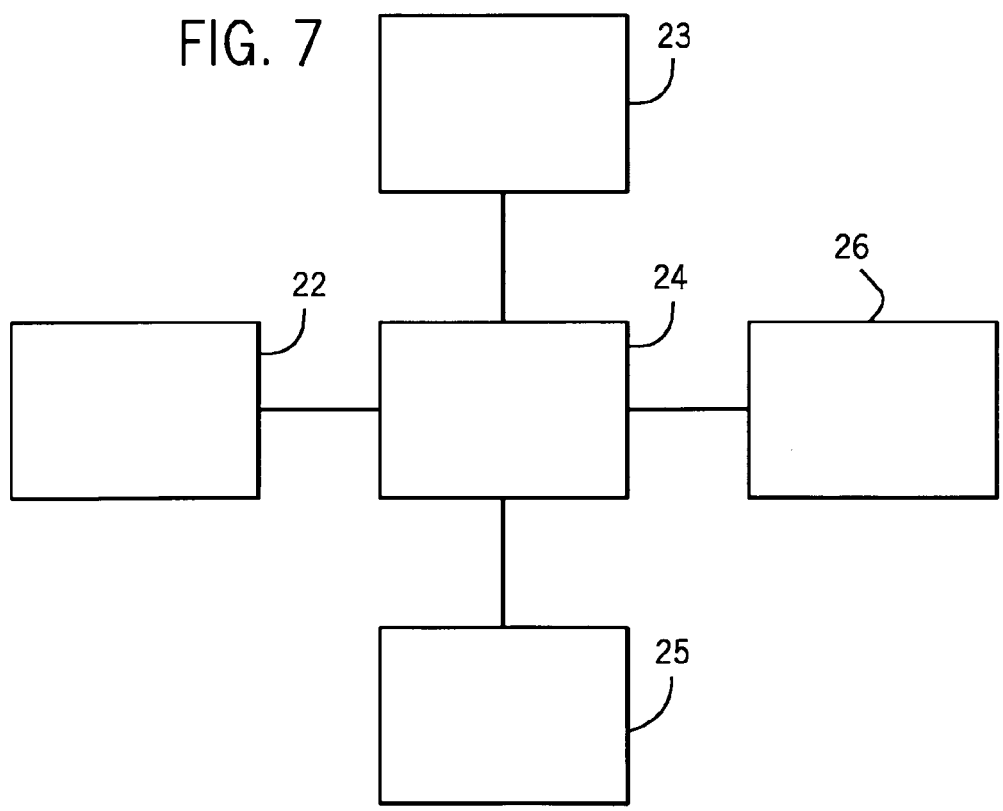
FIG. 7 illustrates an organizational chart of the electronics of the present invention.

The display 23 is in communication with an electronics module 24. FIG. 7 illustrates the components in electrical communication with the electronics module 24. The electronics module 24 operates as a processor, translating signals from a relative humidity sensor 25 into a signal to the display 23. In one embodiment, the electronics module 24 includes a power source such as a battery 26.

The relative humidity sensor 25 is disposed within the tail portion 14. In one embodiment, the relative humidity sensor 25 is located substantially at the detecting end 18 of the tail portion 14 so as to be in operative communication with the environment outside of the probe 10. In one embodiment, best shown in FIG. 2, the aperture 19 is covered by a perforated screen 28. In an exemplary embodiment, a vapor permeable member 30 is provided between the relative humidity sensor 25 and the perforated screen 28 through which the relative humidity sensor 25 is able to detect the water vapor content of the environment outside of the probe.

Figure 6:
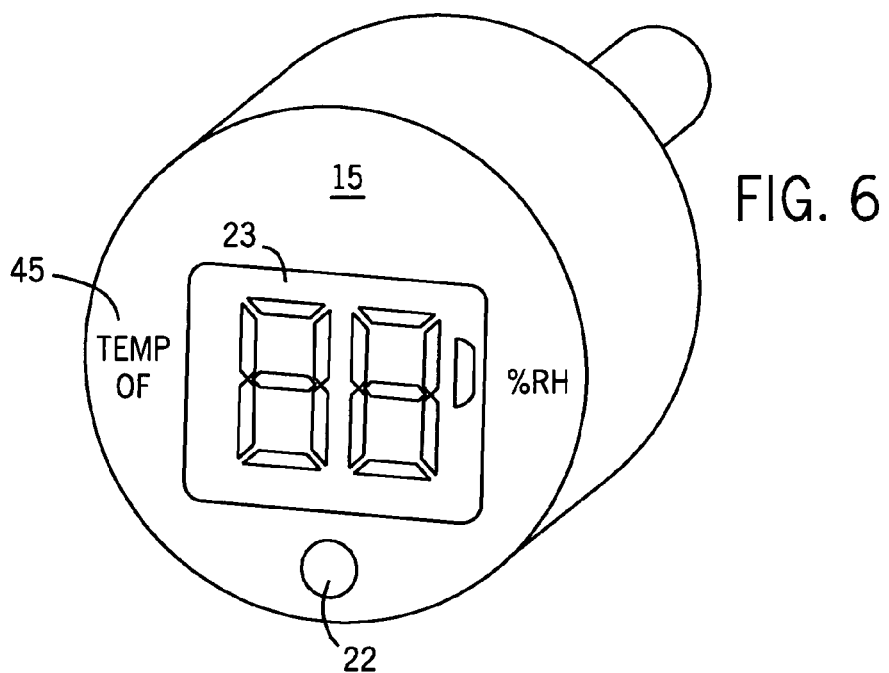
FIG. 6 illustrates a top perspective view of the probe of FIGS. 4 and 5.

In one embodiment shown in FIG. 1, a hollow core 27 is provided within the housing 11. The hollow core 27 runs from the electronics module 24 in the head portion 13 through the tail portion 14 to the detection end 18 forming the aperture 19 therein. In one exemplary embodiment depicted in FIGS. 4-6, a printed circuit board 31 connects the relative humidity sensor 25 with the electronics module 24. In an exemplary embodiment, the printed circuit board is disposed within the hollow core 27. In one embodiment, a battery 26 is provided on one side of the circuit board in electrical communication with the electronics module 24, sensor 25, and display device 23 via the printed circuit 31.

Figure 8:
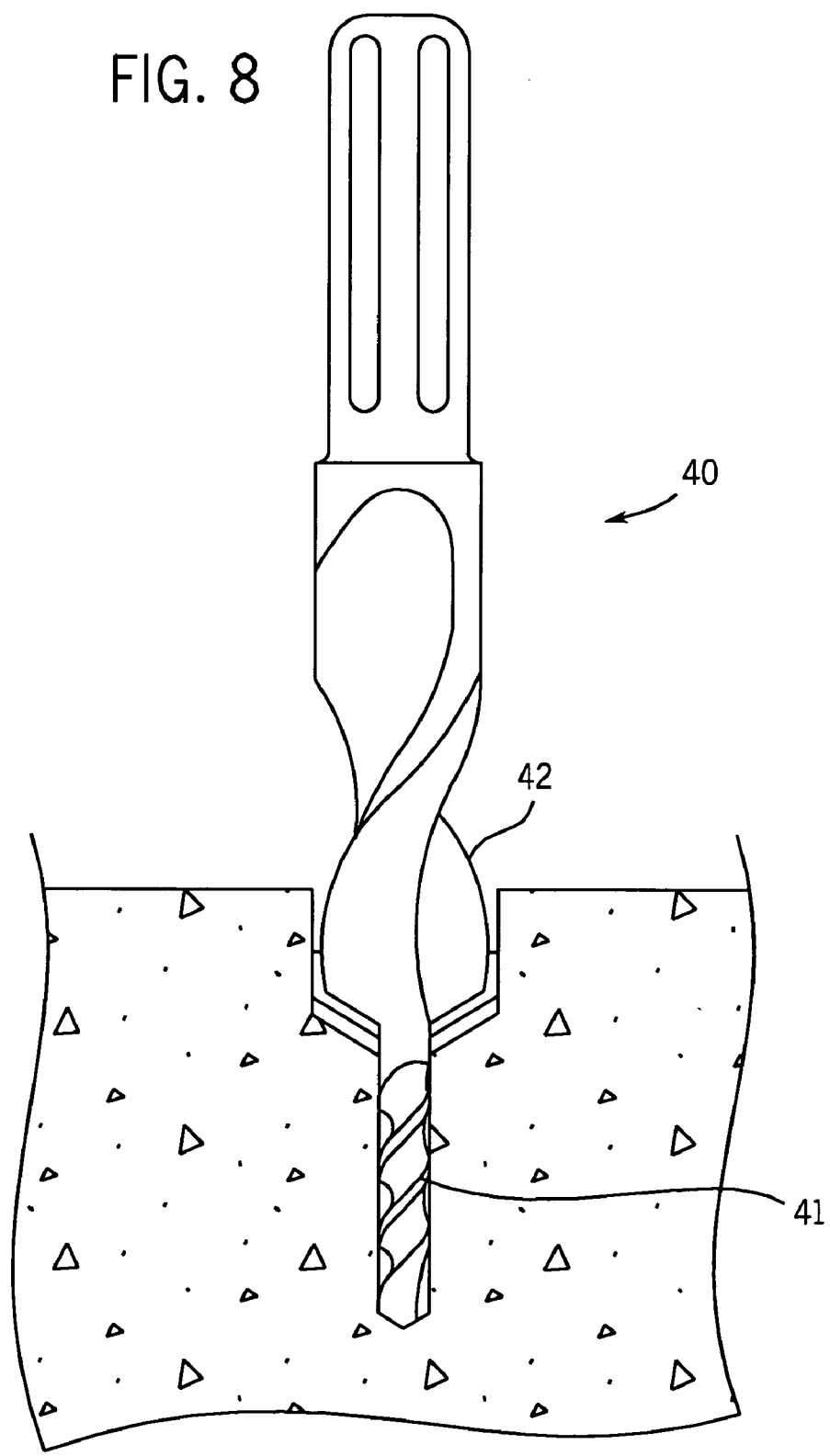
FIG. 8 illustrates a drill bit in accordance with the principles of the present invention.

As shown in FIG. 8, a further aspect of the system of the present invention is directed to a drill bit 40 for boring out a pilot hole and a counterbore into which the probe 10 may be inserted. The drill bit 40 is designed to drill both the pilot hole and counterbore hole at once. The drill bit 40 has a leading tip 41 and a reamer portion 42. The shape and size of the drill bit 40 corresponds to the shape and size of the probe 10.

Figure 9:
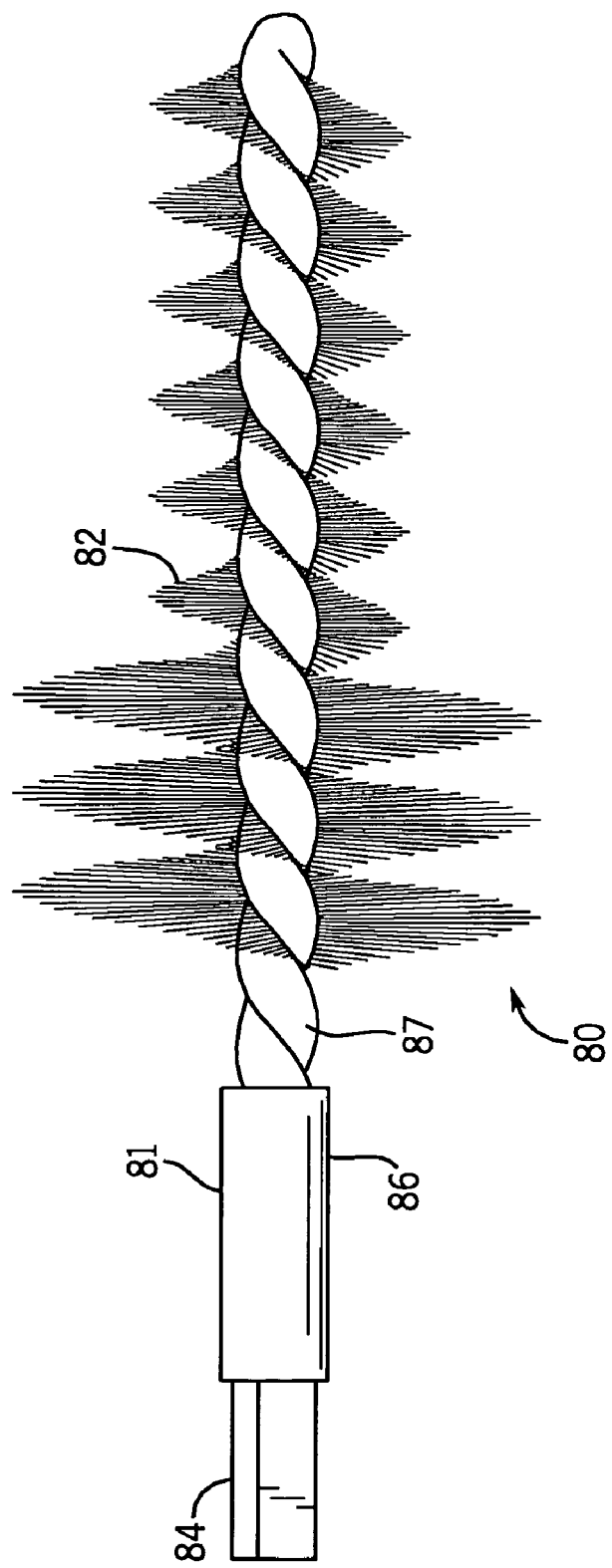
FIG. 9 illustrates a brush attachment for use with the present invention.

A further aspect of the invention relates to a cleaner attachment that permits rapid and thorough cleaning of the drilled hole before inserting the probe 10. As shown in FIG. 9, the cleaner attachment 80 includes a shaft 81 and a brush portion 82. The shaft 81 includes a base portion 84 for engagement with a handle and an upper portion 86 for supporting the brush portion 82. In one embodiment, the upper portion 86 comprises two helically wound strands 87, such as metal wire, of sufficient thickness to provide rigid support. The brush portion 82 comprises strands such as wire, disposed perpendicular to and between the helically wound strands 87. In one embodiment, the brush portion 82 is tapered such as to provide a conical shape when the cleaner attachment 80 is rotated. In use, the cleaner attachment 80 is placed into a drill, inserted in the hole drilled for the probe, and is rotated to remove any debris in the hole. The removal of the debris increases the accuracy of the probe's results and can aid in reducing the time required for the hole to reach equilibrium.

In one embodiment, the present invention relates to a kit including the probe 10, the drill bit 40, and the cleaner attachment 80. These three devices (drill bit 40, brush attachment 80, and probe 10) used in succession, permit a user to quickly drill and clean a hole, insert the probe 10, and obtain accurate relative humidity measurements with only a brief waiting period.

One of ordinary skill in the art will appreciate that the present invention may be used with numerous materials. In a preferred embodiment, the present invention is used for detecting moisture in concrete floor slabs. However, the present invention is suitable for measuring moisture in a variety of construction materials, systems, and structures including, but not limited to:

Concrete building elements such as beams, columns, roof decks, and walls

Pavements, runways, concrete flatwork

Building materials such as exterior insulation and finish systems (EIFS), wall cavities, wood structural elements, gypsum concretes, masonry Use in British Standard BS8203 "Hood Method" now under development in ASTM F06.40.

In one embodiment, the probe 11 can be left embedded in the concrete building element, such as a floor, and reactivated later in the life to measure the moisture condition, for example, if moisture problems appear, or simply to monitor the moisture situation in the building. The probe 11 is designed to be placed below the surface of the material being tested, such as in a bored-out hole. Since it lies totally below the floor surface, or embedded in another element of the building, it is unobtrusive, and not likely to be damaged by traffic or building usage while installed. In an exemplary embodiment, the probe operates in a "standby mode" wherein the device is inactive. A user may activate the probe such as by use of a button on the top of the probe. Upon activation, the probe detects the relative humidity. In one embodiment, a button or mechanism is provided to cycle through the various pieces of information which the probe can display (as previously discussed above). In another embodiment, the display automatically cycles through the various pieces of information pausing for a predetermined time to allow a user to observe the information. In one embodiment, the probe includes a mechanism for automatically deactivating the probe after a predetermined period of time.

In an exemplary preferred embodiment, the present invention contains a mechanism to conserve battery life. In one embodiment, the electronics module 24 includes a mechanism which turns the probe off automatically after a certain time period. A user may turn the probe 10 on by actuating a button 22 on the top of the head portion 13 of the housing 11. In one embodiment, the probe can be connected via a wireless system to a remote location such as by RF signal. In one exemplary embodiment, the probe is adapted to be in communication with a wireless handheld device.

A non-limiting example is provided below to further illustrate aspects and advantages of the present invention. The example is illustrative only and not intended to limit the scope of the invention.

EXAMPLES

A 100-mm thick concrete slab was constructed using a concrete mix typical of commercially-available concrete mixes used for floor slab construction. A hole was drilled in the concrete floor slab using the drill bit 40. The hole was brushed and vacuumed to remove dust, and a probe 10 was inserted. Relative humidity and temperature readings were recorded at intervals by visually observing the display from the probe.

Table 1 lists the results of this experiment, indicating the relative humidity and temperature for sampled times after insertion.

TABLE 1

Experimental Results

| Time After Insertion (Minutes) | Relative Humidity (Percentage) | Temperature (° F.) |
| --- | --- | --- |
| 5 | 82 | 67 |
| 8 | 83 | 67 |
| 10 | 84 | 67 |
| 12 | 84 | 67 |

TABLE 1-continued

Experimental Results

| Time After Insertion (Minutes) | Relative Humidity (Percentage) | Temperature (° F.) |
|---|---|---|
| 14 | 84 | 67 |
| 16 | 85 | 67 |
| 18 | 85 | 67 |
| 20 | 85 | 67 |
| 24 | 85 | 67 |
| 27 | 85 | 67 |
| 30 | 85 | 67 |
| 35 | 85 | 67 |
| 40 | 85 | 67 |
| 45 | 85 | 67 |

Figure 10:
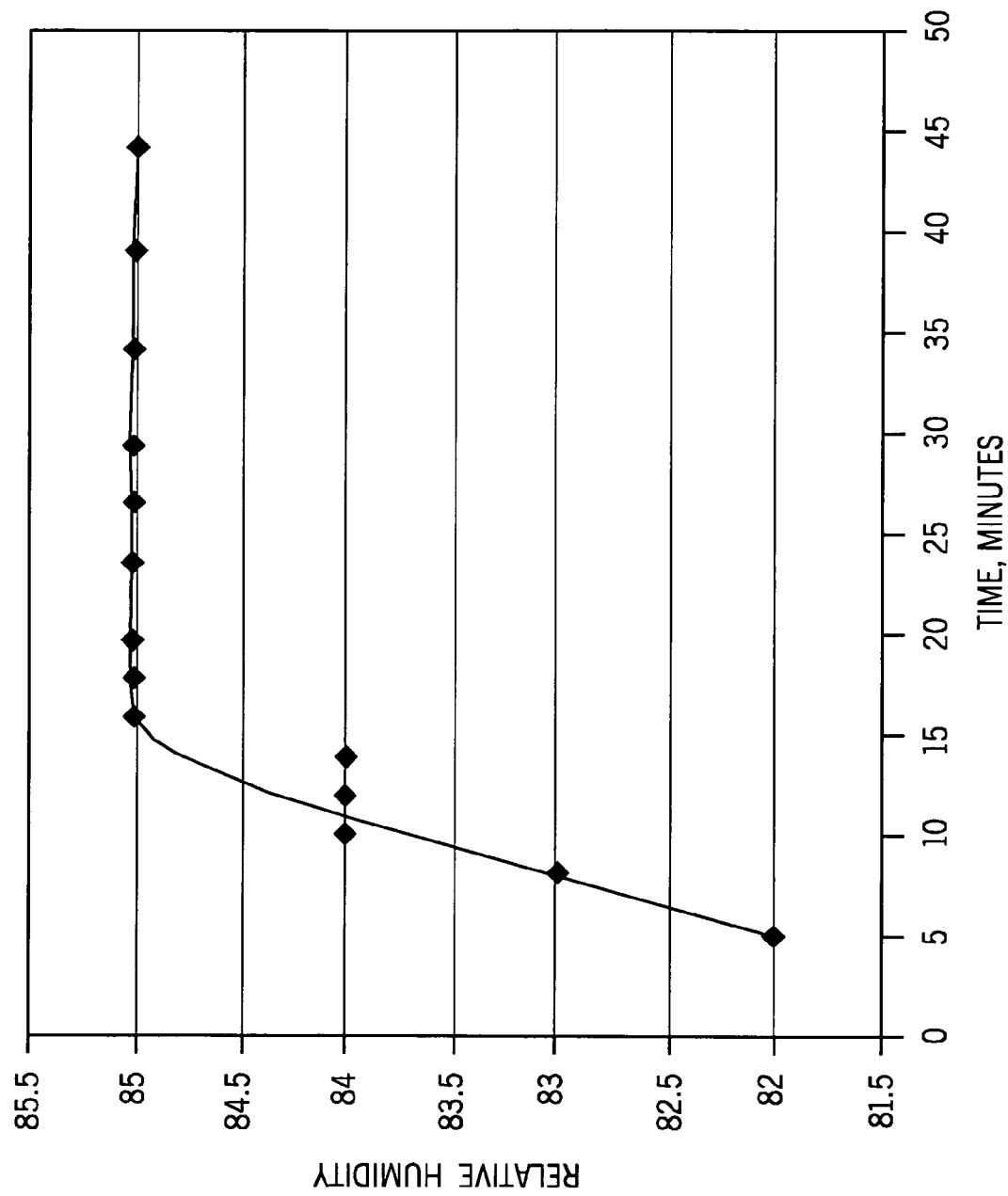
FIG. 10 is a graph depicting the time to equilibrate a device in accordance with the principles of the present invention.

These results are graphed in FIG. 10, as percentage humidity (y-axis) versus time (x-axis). As can be seen both from Table 1 and FIG. 10, the humidity readings equilibrated after 16 minutes and remained so for the remainder of the testing period (45 minutes).

Given the disclosure of the present invention, one versed in the art would appreciate that there may be other embodiments and modifications within the scope and spirit of the invention. Accordingly, all modifications attainable by one versed in the art from the present disclosure within the scope and spirit of the present invention are to be included as further embodiments of the present invention. The scope of the present invention is to be defined as set forth in the following claims.

What is claimed is:

1. A humidity probe for positioning in a hole in a solid for estimating the moisture content of the solid from determination of the relative humidity of the hole, the probe comprising:

a housing having a head portion and a tail portion;

an electronics module disposed within the housing;

a display associated with the head portion and in communication with the electronics module;

the tail portion having an inner chamber and an exterior surface with aperture therethrough;

at least one rib positioned around the perimeter of the housing for engaging a surface defining a perimeter of a hole in a solid;

a relative humidity sensor disposed within the tail portion of the housing proximate the aperture, the relative humidity sensor in operative communication with the electronics module and with an exterior environment, wherein the relative humidity sensor is positioned such that substantially no dead volume exists in the tail portion between the sensor and a volume defined by the solid, the rib, and the external surface of tail portion.

2. The humidity sensor of claim 1, further comprising a vapor permeable membrane disposed between the relative humidity sensor and the exterior environment.

3. The humidity sensor of claim 1, wherein the housing is cylindrical in shape.

4. The humidity sensor of claim 1, wherein the electronics module is disposed within the head portion of the housing.

5. The humidity sensor of claim 4, further comprising a hollow core extending from the electronics module disposed in the head portion through the tail portion further wherein the aperture is formed at an end of the tail.

6. The humidity sensor of claim 1, wherein the circumference of the head portion is substantially larger than the circumference of the tail portion.

7. The humidity sensor of claim 6, further comprising a tapered portion connecting the head portion with the tail portion.

* * * * *